United States Patent [19]

Broersma, Jr. et al.

[11] 4,344,958
[45] Aug. 17, 1982

[54] METHOD OF INHIBITING SICKLING OF SICKLE ERYTHROCYTES USING SUBSTITUTED-2-IMIDAZOLINES

[75] Inventors: Robert J. Broersma, Jr., Noblesville, Ind.; Gayle A. Spittka, Midland, Mich.

[73] Assignee: The Dow Chemical Company, Midland, Mich.

[21] Appl. No.: 200,246

[22] Filed: Oct. 24, 1980

[51] Int. Cl.$^3$ ............................................. A61K 31/415
[52] U.S. Cl. ................................................. 424/273 R
[58] Field of Search ..................................... 424/273 R

[56] References Cited
PUBLICATIONS

Raper, *Ann. Soc. Belge Med. Trop.*, 1969, 49, 2, pp. 205–210.

*Primary Examiner*—Frederick E. Waddell

[57] ABSTRACT

Method for inhibiting the sickling of sickle erythrocytes in blood by contacting the sickle erythrocytes with a compound of the formula:

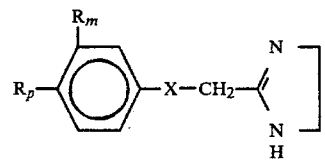

or a pharmaceutically-acceptable salt thereof, wherein X represents sulfur, oxygen or imino; $R_m$ represents chloro, bromo, fluoro or iodo; and $R_p$ represents chloro, bromo, fluoro, iodo, hydroxy, amino or alkyl.

5 Claims, No Drawings

METHOD OF INHIBITING SICKLING OF SICKLE ERYTHROCYTES USING SUBSTITUTED-2-IMIDAZOLINES

BACKGROUND OF THE INVENTION

In the adult human most hemoglobin is hemoglobin A (Hb-A) consisting of two alpha and two beta polypeptide chains. Certain individuals have an abnormal hemoglobin known as hemoglobin S (Hb-S) which results from the hereditary substitution of valine for glutamic acid in the sixth amino acid position in the beta polypeptide chains of hemoglobin. The proportion of Hb-S to Hb-A in such an individual depends upon whether the individual is a homozygous or heterozygous individual. The tendency toward sickling, that is, the formation of abnormally shaped erythrocytes in which the erythrocytes assume a sickle shape, depends upon the amount of Hb-S in the erythrocyte and the level of oxygen tension. Erythrocytes with 100 percent Hb-S sickle at physiological oxygen tensions, however as the amount of Hb-A increases and Hb-S decreases progressively lower oxygen tensions are required to induce sickling. The homozygous individual has 80 to 100 percent of the hemoglobin in the Hb-S form and sickling occurs at ordinary oxygen tensions. Such individuals are said to have sickle cell disease. Heterozygous individuals are said to possess sickle cell trait since only 25 to 40 percent of their hemoglobin is Hb-S, and sickling occurs only at unusually low oxygen tensions.

The presence of sickled erythrocytes can have severe implications since sickled erythrocytes encounter mechanical difficulties in moving through small vessels and the consequent stasis and jamming of these cells can lead to thrombosis and tissue anoxia. In addition, because of the sickled erythrocytes' increased mechanical fragility, hemolysis results. S. L. Robbins and M. Angell, "Basic Pathology", W. B. Saunders Company, Philadelphia, London, Toronto, 1971, pp. 127 and 282.

A treatment or test in which the sickling of red blood cells prone to sickle (sickle erythrocytes) is inhibited or reversed would be useful in the treatment of afflicted individuals or for the study of the sickling phenomenon.

It has been found that certain substituted-2-imidazolines inhibit the sickling in blood of sickle erythrocytes. One of the compounds used in the method of the present invention, 2-((3,4-dichlorophenoxy)methyl)-2-imidazoline hydrochloride has previously been shown to have utility in the treatment of human disorders.

2-((3,4-Dichlorophenoxy)methyl)-2-imidazoline and its pharmaceutically-acceptable salts are known to have antidepressant and barbiturate antagonist activity (White, U.S. Pat. No. 3,449,355) and alcohol antagonist activity (Marshall, U.S. Pat. No. 3,860,719) and activity against minimal brain dysfunction in children (Strande, U.S. Pat. No. 4,141,985). The compound is generically known as "fenmetozole". Fenmetozole hydrochloride has been administered to adult humans, both normal subjects and schizophrenic and/or depressed patients at dosages of 250 to 450 milligrams fenmetozole hydrochloride per day for 3-4 weeks. (Chien and Kaplan, Curr. Therap. Res. 11, 471–474 (1969) and 13, 350–352 (1971)) and has also been administered to normal adults at single dosages ranging from 25 to 250 milligrams with no ill effects other than a "tingling sensation" on the skin reported by some of the subjects, decreased heart rate and increased blood pressure at high dose level, Fink, Curr. Therap. Res. 18, 590–596 (October 1975).

Although 2-((3,4-dichlorophenoxy)methyl)-2-imidazoline hydrochloride has been widely tested, the sickle inhibiting activity of the compound had previously been unknown.

SUMMARY OF THE INVENTION

It has now been discovered that the sickling in blood of red blood cells prone to sickle can be inhibited by contacting the sickle erythrocytes in blood with an effective amount of a compound of the formula:

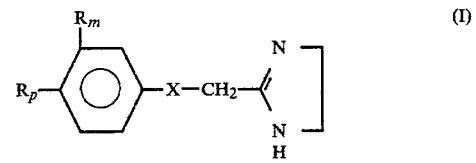

or a pharmaceutically-acceptable salt thereof, wherein X represents sulfur, oxygen or imino (-NH-); $R_m$ represents chloro, bromo, fluoro or iodo; and $R_p$ represents chloro, bromo, fluoro, iodo, hydroxy, amino or alkyl.

As used herein, the term "alkyl" refers to an alkyl group of from 1 to 3 carbon atoms such as methyl, ethyl, propyl and isopropyl.

"Pharmaceutically-acceptable salt" refers to nontoxic acid addition salts of the compounds, the anions of which are relatively innocuous to mammals at exposure levels or dosages consistent with activity or use of the compounds, so that the beneficial effects of the free base are not vitiated by the side effects, or mammalian toxicity, ascribable to the anions. Pharmaceutically-acceptable salts include those derived from mineral acids such as hydrochloric and sulfuric acids and from organic acids such as lactic, maleic, succinic, fumaric, glutaric, citric, malic, p-toluenesulfonic, methanesulfonic and tartaric acids.

As used herein, an effective amount of the compound represented by formula I or a pharmaceutically-acceptable salt thereof is that amount of the compound or its pharmaceutically-acceptable salt which when employed according to the method of the present invention is sufficient to inhibit the sickling of sickle erythrocytes in blood. As used in the specification and claims, "inhibiting" means inhibiting the formation of sickle morphology and also includes actively reversing sickled cells to a more normal or typical morphology, in cases in which sickling has already occurred. The compounds used in the practice of the present invention are therefore particularly useful in the study of the sickling phenomenon, in the investigation of the effects of chemical substances on erythrocytes and has potential usefulness as a treatment for individuals subject to the sickling phenomenon.

DETAILED DESCRIPTION OF THE INVENTION

The compounds used in the practice of the present invention, i.e., the compounds of formula I, or a pharmaceutically-acceptable salt thereof are prepared by reacting the appropriate substituted-phenoxyacetonitrile, substituted-phenylthioacetonitrile or substituted-anilinoacetonitrile represented by the formula:

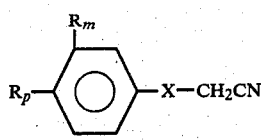

wherein X, $R_m$ and $R_p$ are defined as for formula I, with ethylenediamine p-toluenesulfonate. The reaction is conveniently accomplished employing a procedure similar to that used for the preparation of 2-((halophenoxy)methyl)-2-imidazolines, as described in U.S. Pat. No. 3,449,356. In preparing the 2-imidazoline compounds of formula I, the appropriate acetonitrile, i.e., formula II compound, and the ethylenediamine p-toluenesulfonate are mixed and heated together in an inert organic solvent, such as 1,2-dichlorobenzene for a time sufficient to obtain the desired 2-imidazoline p-toluenesulfonate salt. The reaction is preferably carried out under an inert atmosphere, accomplished by passing nitrogen through the reaction mixture to carry off the ammonia formed during the reaction. The 2-imidazoline p-toluenesulfonate salt can be separated from the reaction mixture using known procedures such as adjustment of reaction mixture concentration, filtration, centrifugation and decantation. The 2-imidazoline p-toluenesulfonate salt can be purified by conventional procedures such as recrystallization and washing.

Alternatively, the 2-imidazoline p-toluenesulfonate salt can be converted to the free base form (i.e., free imidazoline) by hydrolysis in aqueous base. The free base is then separated by extraction with an organic solvent such as methylene chloride ($CH_2Cl_2$) or chloroform ($CHCl_3$), followed by evaporation of the solvent. Purification of the free base is accomplished by conventional methods such as recrystallization or the free base can be converted to a pharmaceutically-acceptable salt by treating the free base with the appropriate organic or mineral acid. The pharmaceutically-acceptable salt can be purified by known procedures such as recrystallization.

The substituted-phenoxyacetonitrile, substituted-phenylthioacetonitrile or substituted-anilinoacetonitrile reactants, illustrated by formula II, are prepared by known procedures, for example, by reacting a substituted-(phenol or phenyl-thiol or aniline) of the formula:

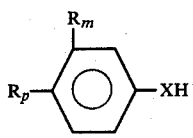

wherein X, $R_m$ and $R_p$ are as defined for formula I, and chloroacetonitrile. The reaction is accomplished by heating the reactants, usually in the presence of a base such as potassium carbonate ($K_2CO_3$) and an inert organic solvent such as dimethylformamide (DMF) or dimethyl sulfoxide (DMSO), for a time sufficient to obtain the desired acetonitrile. Especially in cases where X is -NH-, it may be desirable to simply heat the appropriate formula III compound and chloroacetonitrile neat. The acetonitrile is recovered and purified by conventional procedures such as those described herein.

The following examples are included to further illustrate the invention but are not to be construed as a limitation thereon.

Example 1

2-((3,4-Dichloroanilino)methyl)-2-imidazoline Hydrochloride (a) Preparation of 3,4-dichloroanilinoacetonitrile Chloroacetonitrile (45.3 grams (g)) and 97.2 g of 3,4-dichloroaniline were heated with stirring in a 250 milliliter (ml) round-bottomed three-necked flask at about 120°–125° C. for 2 hours. The reaction mixture was cooled, then diluted with methylene chloride and then filtered to remove the 3,4-dichloroaniline hydrochloride (52.4 g) which had formed. The filtrate was concentrated to dryness under vacuum, leaving a black gummy residue that crystallized on cooling. The residue was put in solution in hot toluene, the solution was then cooled and filtered, which gave 38.3 g of crude product. Recrystallization from cyclohexane gave 36.2 g of purified 3,4-dichloroanilinoacetonitrile as pink crystals, having a melting point (m.p.) of 95°–97° C.

(b) Preparation of 2-((3,4-dichloroanilino)methyl)-2-imidazoline hydrochloride

A mixture of 30.15 g of 3,4-dichloroanilinoacetonitrile and 35.0 g of ethylenediamine p-toluenesulfonate in 110 ml of 1,2-dichlorobenzene was heated at reflux temperature under a small flow of nitrogen for 1.5 hours. The reaction mixture was then cooled and washed with water. The 1,2-dichlorobenzene was concentrated under vacuum and the remaining residue was put in solution in $CH_2Cl_2$ and shaken with dilute sodium hydroxide. The $CH_2Cl_2$ layer was separated and treated with diatomaceous earth and activated charcoal and then filtered. The filtrate was concentrated to dryness under vacuum and the black gummy residue which remained put in solution in isopropyl alcohol. Gaseous HCl was bubbled through the solution resulting in crystal formation. The mixture was cooled and filtered to obtain the product. Recrystallization from absolute ethanol gave 13.0 g of purified 2-((3,4-dichloroanilino)-methyl)-2-imidazoline hydrochloride as tan crystals, m.p. 221°–223° C.

EXAMPLE 2

2-(3,4-Dichlorophenoxy)methyl)-2-imidazoline Hydrochloride (a) Preparation of 3,4-dichlorophenoxyacetonitrile A mixture of 81.5 g of 3,4-dichlorophenol, 98.0 g of anhydrous $K_2CO_3$, 40.0 g of chloroacetonitrile and 100 ml of DMSO was stirred and heated to 70° C. after an initial period of ice cooling. The reaction mixture was heated at 70°–80° C. for 3 hours and the reaction mixture was then poured into 2500 ml of ice and water which resulted in crystal formation. The crystals were removed by filtration, washed with water and then dried overnight in a vacuum oven. The resulting solids were put in approximately 1 liter of boiling cyclohexane and treated with activated charcoal and then filtered. The filtrate was cooled to 10° C. and filtered, which gave 91.5 g of 3,4-dichlorophenoxyacetonitrile, m.p. 61°–62° C.

(b) Preparation of 2-((3,4-dichlorophenoxy)methyl)-2-imidazoline hydrochloride, m.p. 244°–245° C.

The preparation of 2-((3,4-dichlorophenoxy)methyl)-2-imidazoline hydrochloride is described in U.S. Pat. No. 3,449,355. The subject compound was prepared by heating a mixture of 3,4-dichlorophenoxyacetonitrile, ethylenediamine p-toluenesulfonate and 1,2-dichlorobenzene to obtain 2-((3,4-dichlorophenoxy)methyl)-2-imidazoline p-toluenesulfonate. The free base, i.e., 2-((3,4-dichlorophenoxy)methyl)-2-imidazoline was obtained by hydrolyzing the p-toluenesulfonate salt in aqueous base. The subject compound, 2-((3,4-dichlorophenoxy)methyl)-2-imidazoline hydrochloride was obtained by dissolving the free base in isopropyl alcohol and acidifying the alcohol solution with 5 normal (N) hydrochloric acid in isopropyl alcohol.

EXAMPLE 3

2-Chloro-4-(((2-imidazolin-2-yl)methyl)thio)-phenol Hydrochloride

A mixture of 19.95 g of 2-chloro-4-(cyanomethylthio)-phenol, 23.3 g of ethylenediamine p-toluenesulfonate and 75 ml of 1,2-dichlorobenzene was heated at 160°–175° C. with stirring under a small flow of nitrogen for 1.5 hours. After cooling the reaction mixture, the 1,2-dichlorobenzene was decanted off. The residue was slurried in water and $CH_2Cl_2$ and then basified. The $CH_2Cl_2$ layer was separated from the mixture and an insoluble gum obtained. The gum was put in solution in isopropyl alcohol, acidified with hydrochloric acid in isopropyl alcohol and then cooled. The crude product was removed by filtering and recrystallized from isopropyl alcohol. Recrystallized 2-chloro-4-(((2-imidazolin-2-yl)methyl)thio)-phenol hydrochloride was found to have a m.p. of 181°–183° C.

EXAMPLE 4

2-(((4-Amino-3-chlorophenyl)thio)methyl)-2-imidazoline Dihydrochloride

The compound, 2-(((4-amino-3-chlorophenyl)-thio)methyl)-2-imidazoline p-toluenesulfonate was prepared by refluxing a mixture of 2-chloro-4-cyanomethylthioaniline (10 g), ethylenediamine p-toluenesulfonate (12 g) and 1,2-dichlorobenzene (150 ml). The reaction mixture was cooled and most of the 1,2-dichlorobenzene decanted off, leaving a viscous residue. Water and methylene chloride were added to the viscous residue and the mixture basified. The methylene chloride layer was separated and approximately 10 g of viscous residue obtained. The residue was dissolved in dimethoxyethane and 5 N hydrochloric acid in isopropanol added. Recrystallization from absolute ethanol containing HCl and then from dimethoxyethane gave 2-(((4-amino-3-chlorophenyl)thio)methyl)-2-imidazoline dihydrochloride, m.p. 195°–199° C.

In practicing the method of the invention, the imidazoline compounds are brought into contact with sickle erythrocytes, typically by introducing an effective amount of the compound into the blood of a mammal having blood containing erythrocytes subject to sickling. Introducing an effective sickle inhibiting amount of the above-noted compound or pharmaceutically-acceptable salt into the blood of such a mammal can be carried out directly, e.g., by direct addition to blood samples, or indirectly, by administering the compound to the mammal in a manner effective to provide the sickle inhibiting concentration in the blood stream.

The compound or pharmaceutically-acceptable salt thereof would be introduced using a route of administration which provides an effective but non-toxic concentration of the compound in the blood, either by oral ingestion or direct administration as, for example, intravenous infusion or injection. The amount to be administered would vary depending on the compound or pharmaceutically-acceptable salt employed, the type of erythrocyte sickling inhibition or reversal desired, the size and nature of the mammal, and the manner of contacting the blood. When used to inhibit erythrocyte sickling in a mammal, the quantity of compound or pharmaceutically-acceptable salt to be administered in particular instances can be determined by routine procedures, such as studies of the concentration of the compound in the blood obtained at various time intervals after administration, using various methods of administration, and in vitro studies of the anti-sickling effect obtained with various concentrations of the compound in the particular blood in question.

The compounds described herein were tested in an "Oxygen-Affinity Assay" to measure the ability of the compound to influence the Hb-S oxygen affinity. There is a relationship between oxygen binding and Hb-S gelation and thus a measure of oxygen affinity is an index of Hb-S aggregation within the red blood cell. Hemoglobin S polymers decrease the overall oxygen affinity. Thus a return to normal of Hb-S oxygen affinity is a measure of decreased gelation.

For measurements of oxygen equilibria whole Hb-S blood was equilibrated in a tonometer at 37° C. and measurements were made in the presence of a 5 millimolar (mM) or 10 mM concentration of the test compound. The whole blood pH, oxygen tension, and blood $PO_2$ were measured. The percentage of oxygen saturation was plotted against the partial pressure of oxygen (mm Hg). The $P_{50}$ value (oxygen tension at 50% saturation) was determined for each control and treated whole blood sample and the difference ($\Delta P_{50}$) between the control and treated whole blood sample noted. As used herein, a negative $\Delta P_{50}$ represents a change toward a normal Hb-S oxygen affinity and thus is a measure of the test compound's ability to inhibit the sickling of sickle erythrocytes. The results of the Oxygen-Affinity Assays are presented in Table 1.

TABLE 1

| Compound Example Number | Oxygen-Affinity Assay $\Delta P_{50}$ | |
|---|---|---|
| | 10 mM | 5 mM |
| 1 | −12.6 | −9 |
| 2 | −8.0 | −8 |
| 3 | −13.0 | 0 |
| 4 | −10.0 | −9 |

The data in Table 1 shows that all of the test compounds at a 10 mM concentration exhibited a negative $\Delta P_{50}$ which indicates that the test compound inhibited the sickling of sickle erythrocytes. Several of the test compounds also inhibited the sickling of sickle erythrocytes at a 5 mM concentration.

The solubility of deoxyhemoglobin S (Deoxy Hb-S) was determined utilizing substantially the same procedure described by Behe, M. J., Englander, S. W., *Biochemistry* 18: 4196–4201 (1979). Assays were done to determine the equilibrium solubility of Hb-S in the presence of inhibitor (i.e., test compound). To a concentrated solution of Hb-S in 0.1 molar (M) phosphate, at pH 6.86, was added 0.75 M dithionite and a sufficient quantity of a 0.01 M solution of the test compound at pH 6.89 so that the resulting mixture had a 10 millimolar (mM) concentration of the test compound and a pH of 6.89. Test mixtures were placed in a 4 centimeter (cm) length of thin quartz tubing sealed at one end, and then incubated at 37° C. for two hours to achieve gelation, and then re-equilibrated in a water bath (20° C.) for 20 minutes. The quartz tubing containing the test mixture was then placed in a glycerol filled centrifuge tube (topped by a rubber ring to center the quartz tubing) and centrifuged for two hours at 140,000 times gravity. After centrifugation, the quartz tubing was broken above the pelleted gel and the supernatant hemoglobin removed. The concentration of the hemoglobin in the supernatant was determined by measuring the absorbance at 540 nanometers (nm) after a 300-fold dilution with normally oxygenated buffer.

The Relative Solubility is a measure of the ability of the test compound to increase the solubility of deoxyhemoglobin S and is readily determined by comparing the solubility of the treated (i.e., test compound present) sample versus the control (i.e., test compound absent) sample. A Relative Solubility value greater than 1.0 indicates that the deoxyhemoglobin S solubility was greater in the presence of test compound and demonstrates that the test compound was effective in inhibiting sickle erythrocyte hemoglobin gelation. The results of the deoxyhemoglobin S solubility testing are presented in Table 2.

TABLE 2

| Compound Example Number | Solubility of Deoxy Hb-S gm/dL* | | Relative Solubility (gm/dL treated) (gm/dL control) |
|---|---|---|---|
| | Control | Treated | |
| 1 | 18.1 | 21.7 | 1.20 |
| 2 | 18.1 | 20.8 | 1.15 |
| 3 | 18.1 | 20.5 | 1.13 |
| 4 | 18.1 | 19.8 | 1.09 |

*Solubility of deoxyhemoglobin S in grams/deciliter

The data in Table 2 indicates that the solubility of deoxyhemoglobin S was increased in the presence of a 10 mM concentration of the test compound, which demonstrates the effectiveness of the compound in inhibiting sickle erythrocyte hemoglobin gelation.

What is claimed is:

1. A method for inhibiting the sickling of red blood cells prone to sickle in blood containing said cells which comprises introducing into said blood an effective sickle inhibiting amount of a compound of the formula:

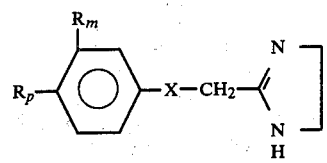

or a pharmaceutically-acceptable salt thereof, wherein X represents sulfur, oxygen or imino; $R_m$ represents chloro, bromo, fluoro or iodo; and $R_p$ represents chloro, bromo, fluoro, iodo, hydroxy, amino or alkyl.

2. The method of claim 1 wherein the compound is 2-((3,4-dichloroanilino)methyl)-2-imidazoline or a pharmaceutically-acceptable salt thereof.

3. The method of claim 1 wherein the compound is 2-((3,4-dichlorophenoxy)methyl)-2-imidazoline or a pharmaceutically-acceptable salt thereof.

4. The method of claim 1 wherein the compound is 2-chloro-4-(((2-imidazolin-2-yl)methyl)thio)-phenol or a pharmaceutically-acceptable salt thereof.

5. The method of claim 1 wherein the compound is 2-(((4-amino-3-chlorophenyl)thio)methyl)-2-imidazoline or a pharmaceutically-acceptable salt thereof.

* * * * *